United States Patent [19]

Doyle

[11] Patent Number: 4,646,739
[45] Date of Patent: Mar. 3, 1987

[54] LAYMAN'S NASAL HEMOSTAT

[76] Inventor: Donald E. Doyle, 9201 Sunset Blvd., Ste. 611, Los Angeles, Calif. 90069

[21] Appl. No.: 832,430

[22] Filed: Feb. 24, 1986

[51] Int. Cl.$^4$ .............................................. A61B 17/12
[52] U.S. Cl. .................................................. 128/325
[58] Field of Search ................ 604/369, 286, 11, 904, 604/1; 128/342, 325

[56] References Cited

U.S. PATENT DOCUMENTS

| | | | |
|---|---|---|---|
| 2,179,964 | 11/1939 | Stevens | 128/342 |
| 4,030,504 | 6/1977 | Doyle | 128/325 |
| 4,568,326 | 2/1986 | Rangaswamy | 604/1 |

Primary Examiner—John D. Yasko

[57] ABSTRACT

A nasal hemostat adapted for insertion into a nasal cavity by individuals not trained in medical or nursing arts is composed of contracted material adapted to expand into a porous tampon upon contact with a fluid. The contracted tampon is in the form of an elongated rectangle. Upon expansion, the tampon assumes the shape of a small, right-angled triangle adjacent to a truncated isosceles triangle, connected by a common top, having a linear top wall and two parallel side walls. Upon expansion, the tampon will apply hemostatic pressure to substantially all parts of the most important area of the nasal cavity in regards to hemorrhage. Furthermore, the shape of the tampon is such that there should be essentially no waste from the raw material used in the manufacture of said tampon, thereby greatly decreasing manufacturing costs and allowing the tampon to be more readily available to the nonmedical public.

3 Claims, 7 Drawing Figures

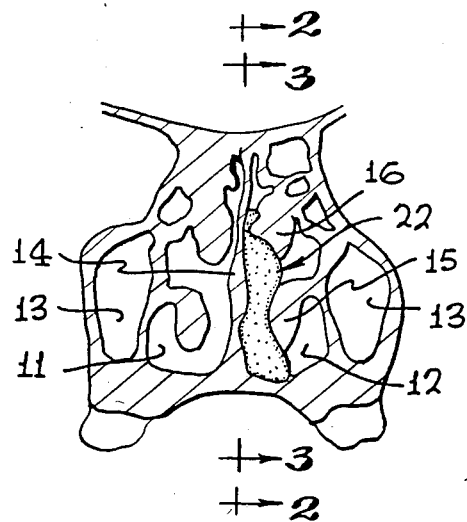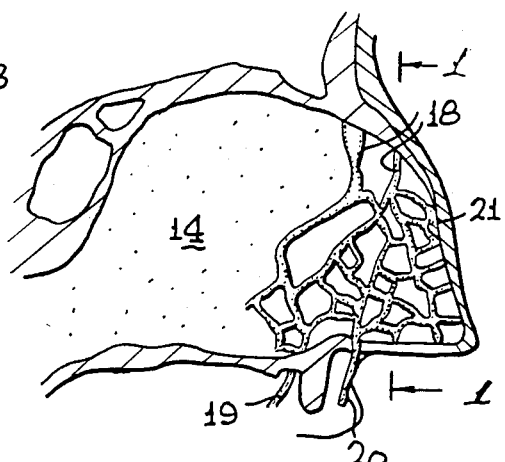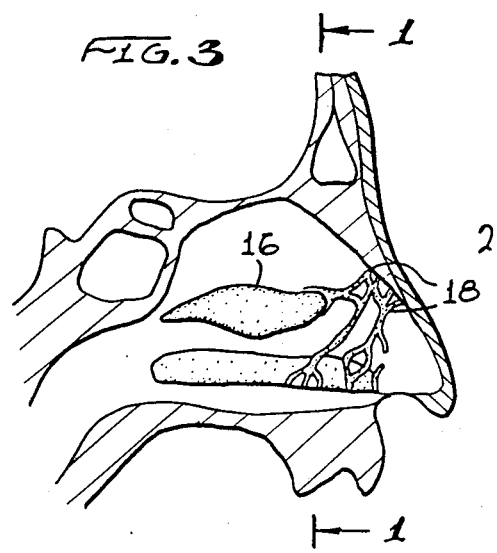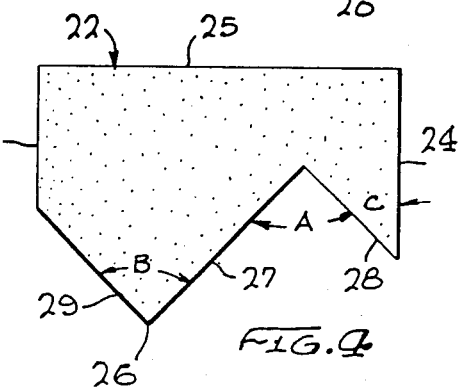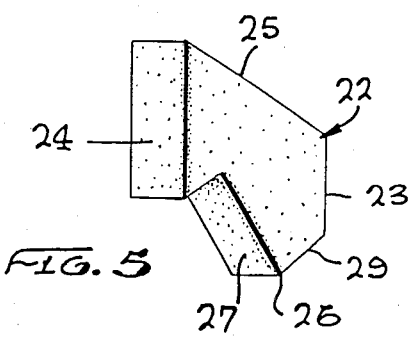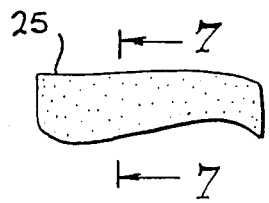

LAYMAN'S NASAL HEMOSTAT

BACKGROUND OF THE INVENTION

This invention relates to hemostats and, particularly, to an apparatus for providing hemostatic pressure to the most important area of the nasal cavity in regards to frequency of nasal hemorrhage.

At present, the various methods of controlling nasal hemorrhage involve devices or a series of devices which require the knowledge, service, and skill of a physician or trained nurse or paramedic for implementation. In our experience as an otolaryngologist, there is no safe method available to the nonphysician or nonmedical individual for emergency control of nasal hemorrhage. Folk medicine and home remedies, long-existing for attempts at controlling nasal hemorrhage are seldom more sophisticated than the placement of a piece of tissue paper into the bleeding site of the nose, and are usually grossly inadequate for the emergency. Moreover, for the nonnasal medical/surgical specialist, the devices presently available generally require skills beyond the scope of even a general practitioner and certainly more than is necessary for the qualified paramedic or nurse.

At present, a plurality of gauze cylinders are forced into the nasal cavity, one after another, until sufficient pressure is created to provide a type of nasal hemostat. Such a procedure is extremely awkward, time-consuming, and painful. In addition, the gauze cylinders frequently fail to apply pressure to the specific blood vessel which has been ruptured. More recently, a type of balloon has been employed to expand in the nasal cavity for the same purpose. While this procedure is less time-consuming and painful, it also is often ineffectual in applying hemostatic pressure to the specific blood vessel which has been ruptured and is certainly beyond the scope of the average individual for its use.

Even more recently, an intranasal tampon designed and patented by your petitioner has appeared in the marketplace, but it, too, admittedly, is beyond the scope of the nonmedical public and even the average general physician.

As a result of our experience with this medical emergency and our recognition that it is extremely rare for an individual to suffer a nosebleed when the immediate services of a trained physician are available, we have designed a nasal hemostat which is, at the same time, both easily utilized by the nonphysician and nonspecialist physician and also extremely effective in the vast majority—that is, greater than 90%—of nosebleeds.

The design of this nasal hemostat was greatly influenced by the desire to diminish the amount of waste material and provide for an interlocking of two like hemostats with total use of a square of all raw material. The triangular shapes interdigitate and form a square, virtually ensuring total use of the raw material.

SUMMARY OF THE INVENTION

A nasal hemostat adapted for insertion into a nasal cavity is composed of a tampon of contracted, expansible material formed to apply pressure against the anterior third of the nasal cavity and all surrounding walls. The expanded tampon thus applies hemostatic pressure to the most important area, Kiesselbach's plexus, the vascular network on the nasal septum, where over 90% of all nosebleeds arise from. In addition, pressure is exerted against the lateral wall of the nose in the anterior one third, thus tamponading the anterior portion of the inferior turbinate, an area where most turbinate bleeding occurs.

In one embodiment of the invention, the expanded tampon has a generally geometric shape, composed of a right-angle triangle and a truncated isosceles triangle connected by a common top, a straight, anterior and top wall, ending in a triangular apex, and two parallel side walls. The smaller of the two triangular elements projects downward from the nostril of the nasal fossa into which the entire hemostat is inserted. It is this smaller triangular portion which the individual grasps to both insert the tampon/hemostat and remove it when appropriate.

DESCRIPTION OF THE DRAWINGS

The invention may best be understood when the drawings are taken in conjunction with the following detailed description, wherein:

FIG. 1 is a cross-sectional, elevational view taken along a transverse, anterior plane of the nose, as indicated by the line 1—1 of FIG. 2 and 1—1 of FIG. 3, showing the nasal hemostat of one embodiment of this invention inserted in one of the nasal cavities;

FIG. 2 is a cross-sectional, elevational view taken along the line of 2—2 of FIG. 1, showing the nasal septum and some of the major arteries carried by the septum;

FIG. 3 is a cross-sectional, elevational view taken along the line 3—3 of FIG. 1, showing the lateral wall of the nasal cavity and some of the major arteries carried by the anterolateral wall;

FIG. 4 is an elevational view of the nasal hemostat of one embodiment of this invention in expanded form;

FIG. 5 is a three-dimensional representation of the nasal hemostat in expanded form as it would be seen from an angulated frontal view;

FIG. 6 is an elevational view of the nasal hemostat of FIG. 4 and FIG. 5 in contracted form; and FIG. 7 is a cross-sectional, elevational view taken along the line 7—7 of FIG. 6.

DETAILED DESCRIPTION

A contoured tampon is composed of a compressed, porous material adapted to be positioned in a nasal cavity in its anterior portion and to expand upon being contacted with a fluid to thus apply hemostatic pressure to the most important vascular structures and interior parts of the nasal cavity as it relates to nasal hemorrhage. The tampon, when expanded outside the nasal cavity, is generally (a right angle and a truncated isosceles triangle connected by a common top) bitriangular in shape, having a linear top wall, a bi-angular bottom wall, two parallel sides, and is, in essence, a right-angle triangle touching immediately adjacent with the angle of a truncated isosceles triangle, both supported by a common top which is linear and has flat walls.

More specifically, FIG. 1 is a transverse, cross-sectional, elevational view of the nose structure, showing two nasal cavities 11 and 12 and various adjacent sinus cavities 13. Each nasal cavity has two side walls converging at the top of the cavity and a bottom wall, forming the floor of the cavity. An anatomical partition, the nasal septum 14, separates the two nasal cavities and carries upon its surface a plexus of vessels made up primarily of branches of the anterior ethmoidal artery 18, the anterior palatine artery 19, and the superior septal branch of the labial artery 20. In addition, there are two blood vessel-containing structures, the inferior turbinate 15 and the middle turbinate 16, upon which branches of the anterior ethmoidal artery course FIG. 3. The vascular plexus diagramatically represented in FIG. 2 is the area called Kiesselbach's plexus, or Little's area, which comprises the blood vessels responsible for greater than 90% of all nasal hemorrhages in the human being. In addition, a smaller, but important percentage of nasal hemorrhages are seen to occur at the most forward tip of the inferior turbinate 15 and the middle turbinate 16 due to the presence on its surfaces of branches of the anterior ethmoidal artery 18.

In order to allow for the nonphysician or layman an opportunity to control this nasal hemorrhage, especially when the services of a trained physician are not immediately accessible, we have designed a specifically shaped nasal tampon FIG. 4 and FIG. 5, which, when contracted FIG. 6 and FIG. 7, may be easily inserted into a nasal cavity 11 in its contracted shape and expanded upon contact with a fluid to assume that configuration noted in FIG. 4 and FIG. 5, producing a tamponade effect upon both Kiesselbach's plexus 21 and branches of the anterior ethmoidal artery 18, the anterior palatine artery 19, and the septal branch of the labial artery 20.

The nasal hemostat of one embodiment of this invention is shown in the form of an expanded tampon 22 in FIG. 4 and FIG. 5 In this embodiment of the invention, the tampon is composed of a hydrocellulose material which expands in all directions upon contact with a fluid, such as mucus or blood or a saline or water solution. In order to form such a tampon, a unit of expanded and dry hydrocellulose is cut by stamping or the like. The exact dimensions of the contracted tampon may vary depending upon the size of the individual nasal cavity; however, most tampons will be substantially the same shape, having a linear top with parallel sides and a bottom of a greater and lesser triangle, the greater triangle being truncated.

In the embodiment of the invention shown in FIG. 4 and FIG. 5, which is proportioned for an adult nasal cavity, the distance between the anterior and posterior ends 24 and 23 of the expanded dry tampon, after forming, is about 40 mm. The distance between the top wall 25 and the greatest height of the triangle is about 25 mm. Specifically, in referring to FIG. 4 and FIG. 5, the top wall 25 should be approximately 40 mm.; the anterior wall 24, 20 mm. arising from the top wall 25 at a 90-degree angle. At the bottom of the anterior wall 24, at a 45-degree angle C, a hypotenuse 28 extends to meet angle A at 90 degrees, and a second hypotenuse 27. Wall 27 extends posterior and inferiorly for approximately 28 mm., ending at angle B, another 90-degree angle, and posterior hypotenuse 29. 29 extends from angle B for approximately 20 mm. to meet the posterior wall 23, which is also 20 mm. in height. 23 the posterior wall meets with the top wall 25 to form another 90-degree angle.

When contracted and compressed, the nasal hemostat device will be essentially a thin rectangle compressed in all directions.

For utilization, an individual inserts the device into the bleeding nostril with the posterior wall entering the nostril first 23 until all but that portion extending from angle A anteriorly is within the nasal cavity. At this point, contact with blood and mucus will begin expansion of the tampon. In order to facilitate expansion, the individual will place water or saline or even a hemostatic solution, such as Neo-Synephrine, onto the tampon. One of the additional and very important advantages of this particular tampon design is that it may be inserted either correctly, exactly, or upside down, and, because of the configuration FIG. 4 and FIG. 5, the eventual result will be the same; that is, a tampon conforming to the essentially triangular dimensions of the anterior nasal fossa, causing lateral and medial pressure, specifically, medially against Kiesselbach's plexus 21.

Another key point and advantage of this particular embodiment of the tampon design is that when inserted and expanded, the angle A of the tampon will straddle either the inferior sill of the nostril or the superior lip of the nostril, thereby making it unlikely that the entire tampon would be aspirated into the nasal fossa, making it difficult for the individual to remove. In our knowledge, such an advantageous design element does not exist in prior designs of nasal tampons.

At this point, the individual may either seek the further services of a physician, once the emergency is under control, or may elect to wait two hours and remove the device themselves by grasping that portion which had not entered the nostril and gently extracting the device.

I claim:

1. A nasal hemostat adapted for insertion into a naval cavity by a nonmedically trained or medically trained individual comprising:
    a two-element tampon of contracted material adapted to be expanded upon contact with a fluid, said tampon, prior to contraction, initially having a generally geometric shape composed of a small right-angled triangle element and a larger truncated isosceles triangle element ending in a triangular apex connected by a common top, a straight anterior and top wall and two parallel side walls; the smaller right-angles triangle element of the two triangular elements projects downward from the nostril of the nasal fossa into which the entire hemostat is inserted so as to bear against the superior septal branch of the labial artery thereby producing a safety mechanism against aspiration; and
    said smaller right-angled triangle element having an apex shorter than the apex of said other triangle element.

2. The invention as defined in claim 1 wherein:
    said geometric shape including said two triangular elements adapted to expand to provide tamponading pressure against selected areas of the nasal cavity in the production of epistaxis for control purposes.

3. The invention as defined in claim 1 wherein:
    said top wall or one of said side walls defining said truncated isosceles triangles respectively so as to form fit and be conformal with the natural shape of the nasal cavity occupies by said tampon whereby exerted pressure bears against the ethmoidal artery.

* * * * *